United States Patent [19]
Carson

[11] 4,217,891
[45] Aug. 19, 1980

[54] NOVEL ARTHROSCOPE

[76] Inventor: Robert W. Carson, 1419 Circle Way, Salt Lake City, Utah 84103

[21] Appl. No.: 861,632

[22] Filed: Dec. 19, 1977

Related U.S. Application Data

[63] Continuation-in-part of Ser. No. 806,833, Jun. 15, 1977.

[51] Int. Cl.³ .............................................. A61B 1/06
[52] U.S. Cl. ........................................................ 128/6
[58] Field of Search .................. 128/4, 5, 6, 7, 8, 9, 128/10, 351, 303.15

[56] References Cited

U.S. PATENT DOCUMENTS

| | | | |
|---|---|---|---|
| 1,703,216 | 2/1929 | Wappler | 128/6 |
| 1,747,407 | 2/1930 | Wappler | 128/6 |
| 2,120,996 | 6/1938 | Wappler | 128/7 |
| 3,799,150 | 3/1974 | Bonnet | 128/6 |
| 4,024,858 | 5/1977 | Chikama | 128/4 |

FOREIGN PATENT DOCUMENTS 719538 12/1954 United Kingdom ................. 128/6

*Primary Examiner*—Richard J. Johnson
*Attorney, Agent, or Firm*—Trask & Britt

[57] ABSTRACT

An arthroscope is constructed within a sheath having a cross-sectional configuration generally rectilinear, but with the longer sides slightly arcuate. The dimension of the sheath along the minor axis of its cross-section is as small as possible to accommodate the systems, e.g., lens, irrigation, instrument channel, included in the instrument. The radius of curvature of the arcuate sides is selected to approximately match the contours of the joint bones of interest, e.g., the femoral condyles and the tibial plateaus.

20 Claims, 7 Drawing Figures

NOVEL ARTHROSCOPE

RELATED PATENT APPLICATIONS

This application is a continuation-in-part of Ser. No. 806,833, filed June 15, 1977, entitled "Arthroscopic Surgical Apparatus and Method". The parent application discloses apparatus and methods useful for arthroscopic examinations and surgical procedures. The apparatus described and claimed herein finds use in conjunction with the apparatus and methods of the parent application, the disclosure of which is incorporated by reference.

BACKGROUND OF THE INVENTION

1. Field

This invention pertains to endoscopes in general and to arthroscopes in particular. Specifically, it provides such an instrument in a configuration ideal for use in arthroscopy.

2. State of the Art

Endoscopy is the art of examining the interior of a body cavity or hollow organ by the use of a slender tubular telescopic instrument called an "endoscope". Endoscopes have been in common use since the early twentieth century. These instruments include a lens system, which may be conventional glass lenses within a rigid tube, air spaces between glass rods shaped to configurate the entrapped air pockets as lenses, optical glass fibers combined with conventional lenses, or other means; and a lighting system, which may be a direct illumination system (e.g., a tungsten light bulb) but is more often fiber light (light transferred from an external source through optical glass fibers). Endoscopes also commonly contain an irrigation system for introducing fluids, typically normal saline solution, to the region being examined. These systems are all contained within a cylindrical tubular housing, usually called a "sheath", which may be flexible, but is more often rigid. The cross-sectional configuration of the sheath normal its longitudinal axis (that is, as viewed from the distal end of the endoscope) is traditionally circular.

Examples of modern endoscopes are disclosed by U.S. Pat. Nos. 3,525,332; 3,599,630; 3,608,547; 3,730,632; 3,744,906; 3,818,902; 3,819,267; and 3,889,662.

Endoscopes have been used for arthroscopic examinations for several decades. The development of arthroscopy and instruments adopted for arthroscopic examinations (arthroscopes) is described in the monograph "Arthroscopy of the Knee", Robert W. Jackson and David J. Dandy, Modern Orthopedic Monographs, 1976 Grune & Stratton, Inc., New York. From the monograph, it is apparent that the principal objective sought in developing arthroscopes has been to reduce their diameter compared to earlier endoscopes. All of the components conventional to an endoscope, namely an optical system, a lighting system, an irrigation system, and often an instrument channel, are contained within a usually rigid cylindrical sheath of approximately circular cross-section. The Watanabe 22 shown in FIGS. 2-5 of the monograph utilizes a sheath slightly oval in cross-section to accommodate two crescentic bundles of light fibers for illumination. The grouping of the light fibers in this fashion is to avoid the penumbra typically present in the center of the visual field.

Examination of the knee joint, or other joints, imposes certain restrictions on procedures not normally encountered with other endoscopic examinations. For example, a persistent problem in arthroscopy has been maintaining adequate sterility. A circular cross-section is appropriate for introducing into the orifices of the genitourinary and gastrointestinal tracts or for puncturing the abdominal wall, but the introduction of conventional round arthroscopes to the knee joint tends to be traumatic because of the limited spacing between bones. Conventional arthroscopes of small cross-section are susceptible of breakage if the knee is flexed or if too much force is applied in efforts to distract the joint using the arthroscope as a lever or fulcrum. In the past, less delicate arthroscopes have necessarily been constructed within sheaths of greater diameter.

SUMMARY OF THE INVENTION

The arthroscope of this invention departs substantially from the structural concepts traditional to endoscopes. The instrument provides the necessary components for examination (lens system, light system and usually an irrigation system) within a sheath housing having a cross-sectional configuration (taken normal the major axis of the arthroscope) which is neither circular nor oval but is shaped as either a parallelogram or a modified parallelogram with a pair of approximately parallel longer sides and a pair of shorter sides which may also, but need not be parallel. The aforedescribed cross-sectional configuration is perceived by viewing the arthroscope from its distal end. Of substantial importance is that the spacing between the longer sides (referred to as the "thickness" of the instrument) be as small as possible, having due regard to the space requirements of the components within the sheath. In a diagnostic arthroscope, the component of largest diameter is usually the lens system. The cross-sectional spacing between the longest sides of the sheath need then be just sufficient to accommodate this component. Operating arthroscopes sometimes require larger sheaths to accommodate an instrument channel of greater diameter than the lens system.

The longer sides, while generally parallel or approximately parallel, are desirably arcuate with a radius of curvature selected to approximately match the bones of the joint undergoing examination. In most instances, when the longer sides are arcuate, one side wall is concave and the other is convex, although it is possible for those side walls to be either mutually concave or convex. The radius of curvature selected will necessarily vary according to the construction of the joint of interest, size of the individual patient, and other factors. In practice, however, a radius of curvature between about two and about three centimeters is generally appropriate for large joints such as the knee, hip and shoulder joints. A radius of about 2½ centimeters is presently regarded as ideal for an instrument intended for general purpose applications.

Although the instruments of this invention are purposely constructed as thin as possible, the spacing between the short sides of the cross-section, (referred to as the "width" of the instrument) may be relatively large. That is, considerable freedom of width is permissible to accommodate a number of structural features not available with conventional arthroscopes. By way of illustration, the width of the instrument may be enlarged to accommodate additional optic fibers, if greater brilliance at the operational site is desired. This feature has application in instruments adapted for photography or to incorporate teaching attachments, for example. For most applications, adequate lighting is provided when the cross-sectional area of the optic fibers in the sheath approximately equals the cross-sectional area of the objective lens. Freedom of width also permits adaption of the distal end of the arthroscope as a retractor to move the synovium or the fat pad aside. Moreover, the instrument channel may be shaped to pass relatively wide instruments, thereby obviating one of the limitations heretofore imposed on the design of surgical instruments used with arthroscopes.

One of the inherent difficulties of mastering arthroscopic techniques has been the lack of depth preception provided by conventional arthroscopes. The increased width permitted by the present invention offers two means for improving on this situation. First, depth perception and perspective at the operative site is enhanced by increasing the lateral spacing of the objective lens from the distal termination of the instrument channel. The surgeon thus observes the instrument approaching the operative site at an angle rather than directly in his line of sight. Second, it is within contemplation to mount a second lens system within the sheath, thereby providing true binocular vision. Either or both of these expedients will enable many more surgeons to become skilled at arthroscopic surgery, and should also permit the development of more intricate diagnostic and surgical procedures.

Of paramount importance, the "thinness" of the arthroscopes of this invention permits more thorough examination of joints with greater accuracy. The potential for false negative readings is greatly reduced. (A "negative" reading means that nothing wrong is observed. ) When the arcuate shape hereinbefore described is incorporated, both diagnostic and surgical procedures are further facilitated. The claimed arthroscopes often can probe to the interior of a joint without mechanically distracting the joint as in current practice.

The aforedescribed advantages are achieved with an attendant reduction of trauma to the patient. First, the soft tissues must be penetrated to gain access to the joint space suffer markedly reduced trauma through use of this invention. Of even greater significance, from the standpoint of present experience in the art, the present invention causes less trauma to the cartilage surface of the joint. In those instances when the tip of the arthroscope is used as a fulcrum, e.g., to pry open the back of a knee joint, the forces are spread over a larger surface area, thereby avoiding damage both to the cartilage and the instrument. The sheath of the claimed arthroscopes may be thicker than is now conventional. Moreover, it is practical to contour and polish the sheath exterior to avoid laceration of the cartilage surfaces.

BRIEF DESCRIPTION OF THE DRAWINGS

In the drawings, which illustrate what is presently regarded as the best mode for carrying out the invention.

DESCRIPTION OF THE ILLUSTRATED EMBODIMENTS

Figure 1:
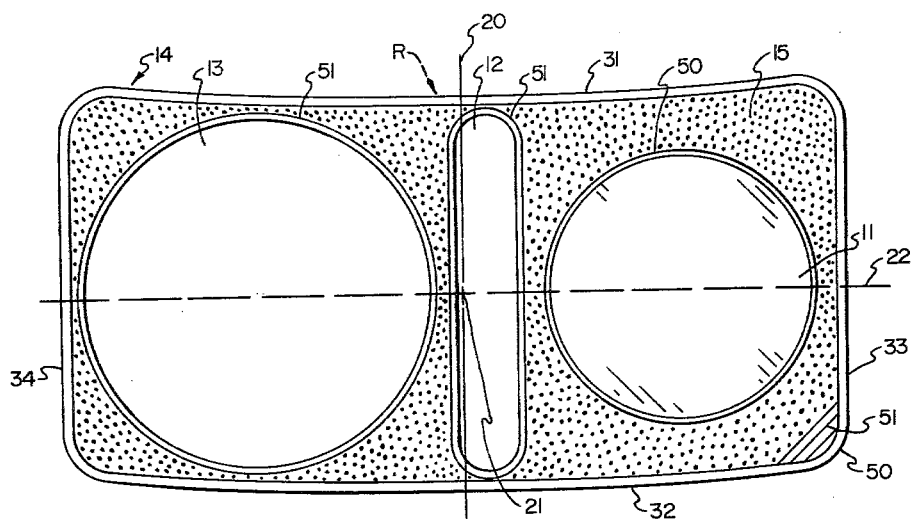
FIG. 1 is a typical operating arthroscope of this invention viewed from its distal end and showing the arrangement of its components.

The operating arthroscope illustrated by FIG. 1 comprises a lens system, the objective lens 11 of which is visible from the distal end of the instrument; an irrigation system, including the conduit 12; and an instrument channel 13; arranged within a rigid sheath 14. The interstitial spaces between the components 11, 12 and 13 and within the sheath 14 are packed with light-transmitting optic fibers 15.

The arthroscope of FIG. 1 is constructed in generally conventional fashion except for the cross-sectional shape of the sheath 14 and the arrangement of the components 11, 12, 13 and 15 housed within the sheath 14. As viewed from its distal end, the cross-section of the arthroscope may be considered as having a minor axis, represented by line 20, which intersects its geometric center 21; and a major axis, represented by the line 22, normal the minor axis 21 at the center 21. The distal ends of instruments with regular cross-sections will be bisected into two congruent parts by the minor axis 20 as shown.

The sheath 14 is of rigid, e.g., stainless steel, construction, and includes two relatively long side walls 31, 32 and two relatively short side walls 33, 34. The side walls 31, 32 which intersect the minor axis 20 are approximately parallel. Ideally, these side walls 31, 32 are arcuate, as shown, to approximately match the surface contours of the bones in a joint. In the illustrated instance, the radius of curvature R is approximately 2.5 centimeters, side wall 31 is concave and side wall 32 is convex. The short side walls 33, 34 may also be approximately parallel, as shown, and are ideally as short as possible; usually just long enough to provide the minimum spacing required between the side walls 31 and 32 to contain the largest system housed in the sheath 14 (the instrument channel 13, FIG. 1; or the lense system 41, FIG. 2).

The width (that is, the spacing of the side walls 33 and 34), of the instrument is selected to provide adequate cross-sectional area for the irrigation system (water channels 12, FIG. 1 and 42, FIG. 2) desired; the lighting system (optical fibers 15, FIG. 1 and 45, FIG. 2); and any other systems which may be included within the sheath.

For applications requiring greater strength, the corners 50 connecting side walls, e.g., 32 and 33, may be structurally reinforced, e.g., by thickening the sheath as shown 51. The lenses 11, 41 are shown contained within rigid tubes 50, e.g., of structural plastic or metal. The various channels, 12, 13, 42 are typically defined by similar rigid tubes or conduit 51.

EXAMPLE I

The operating arthroscope illustrated by FIG. 1 may be constructed within a sheath 14 measuring about 3½ by about 7 millimeters in cross-section to house a lens system with a 2.5 mm objective lense 11, a 3 mm instrument channel 13, a generous water channel 12, and ample optical fibers 15.

EXAMPLE II

Figure 2:
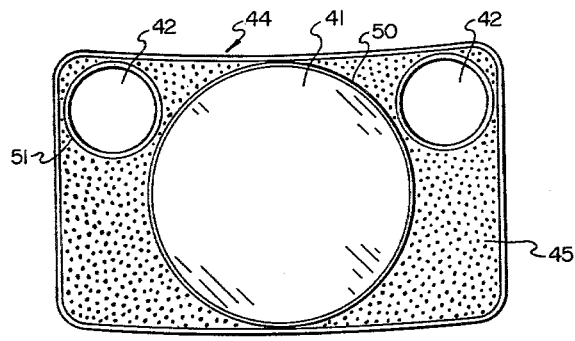
FIG. 2 is a similar view of a typical diagnostic arthroscope of this invention.

The diagnostic instrument shown by FIG. 2 may be constructed within a sheath 44 measuring approximately 2½ by about 4 millimeters. The lens system in such an instrument could have an objective lens 41 as large as about b 2.2 mm.

EXAMPLE III

Figure 3:
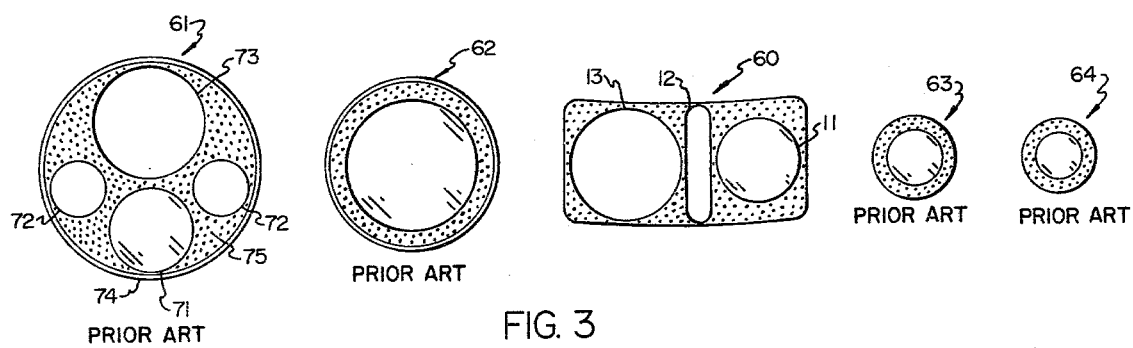
FIG. 3 is a similar view of the arthroscope of FIG. 1 together with a series of prior art instruments drawn to the same scale.

FIG. 3 compares the relative cross-sections of an instrument 60 constructed as shown in FIG. 1 and described in EXAMPLE I with a series 61, 62, 63 and 64 of conventional instruments in current use. By way of comparison, the currently used instrument 61 (a Wolf operating arthroscope) contains a 2.5 mm objective lens 71, a 3 mm instrument channel 72 and a pair of irrigation channels 73 within a circular cylindrical sheath 74 packed with sufficient optic fiber 75 to provide adequate illumination. The sheath 74 is 6.5 mm in diameter. The thickness of the instrument of EXAMPLE I is only slightly over half (about 54%) the diameter of the comparable Wolf instrument, and provides for better irrigation at the operative site. The cross-sectional area of the instrument of EXAMPLE I is also significantly (more than 20%) smaller, thereby requiring a smaller puncture wound for insertion.

The other instruments 62, 63, 64 illustrated by FIG. 3 have diameters 5, 2.5 and 2.2 millimeters, respectively, but include neither instrument nor irrigation channels. These instruments include only lenses and optical fiber lighting systems, and are useful for diagnostic applications only.

Figure 4:
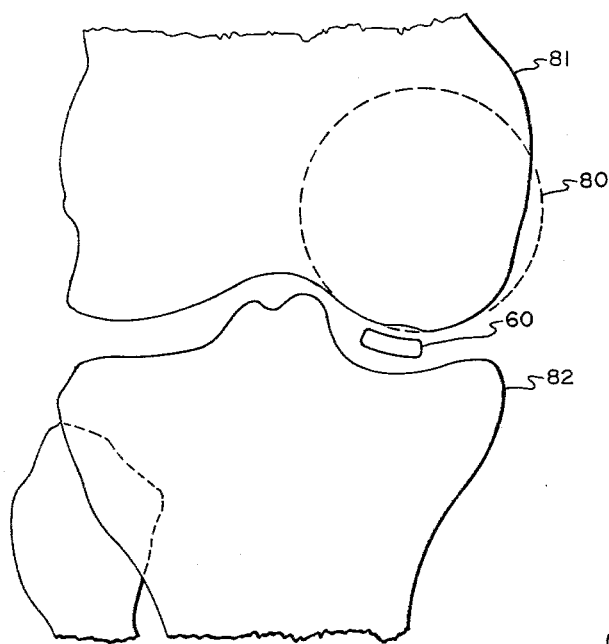
FIGS. 4 through 6 illustrate various joints with an arthroscope of this invention in place.
Figure 5:
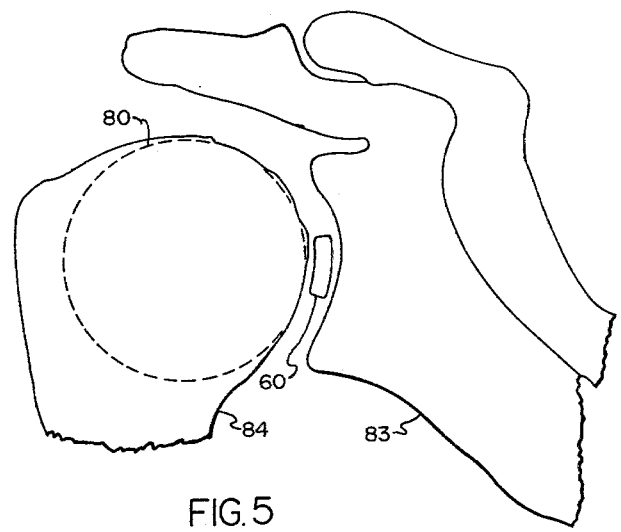
Figure 6:
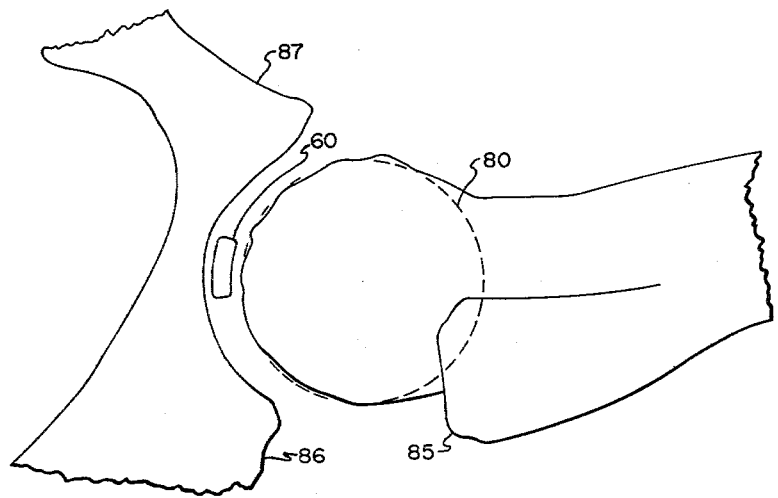

FIGS. 4, 5 and 6 illustrate the placement of an arthroscope 60, constructed as taught by Example I, within a knee joint, shoulder joint and hip joint, respectively. The joints are shown in connection with a reference circle 80. Typical mature joints from the same male individual are illustrated compared to a reference circle with a radius of approximately 2½ centimeters. Of course, the joint of various individuals differ somewhat in size and configuration. Nevertheless, as may be seen from the drawings, a single arthroscope of standardized dimension can be used in all of the major joints of the majority of the human population.

Within tolerable limits, the sockets defined by the femur 81 and tibia 82 of the knee; the scapula 83 and humerus 84 of the shoulder; and the femur 85, ilium 86 and pubis 87 of the hip are generally similar in configuration in a given individual. Accordingly, relatively few arthroscopic instruments constructed in accordance with this invention are sufficient for a complete diagnostic and treatment service of these joints.

Although this disclosure has been directed specifically to arthroscopes and arthroscopy, with specific reference to certain illustrated embodiments, it is not intended to thereby limit the scope of the appended claims. It is within contemplation that the improvements disclosed and claimed herein may be adapted to endoscopes of various types. It is also contemplated that the teachings of this disclosure will lead directly to the development of practical instruments for the improved examination of smaller joints, such as those of the hands or feet. In such instruments, certain design changes, such as the desired radii of curvature for the arcuate side walls of the sheath, are expected. It is also within contemplation that the lens system be adapted to provide a line of sight divergent from the central longitudinal axis of the sheath. An arthroscope in a sheath shaped as in FIGS. 1 and 2, for example, may be provided with a lens system presenting a line of sight canted about 20° toward the concave surface.

Figure 7:
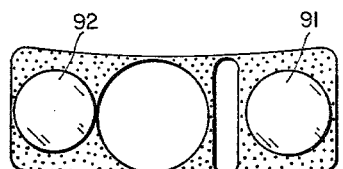
FIG. 7 is a binocular version of an operating arthroscope of this invention viewed from its distal end.

The binocular version illustrated by FIG. 7 includes a pair 91, 92 of lens systems.

I claim:

1. In an arthroscope with structural elements including an optical system and a lighting system fixed within a rigid sheath, the improvement which comprises providing said sheath with a cross-sectional configuration, as viewed from its distal end, having major and minor axes intersecting at the geometric center of said cross-section, wherein the dimension of the cross-section of the interior of the sheath along the said minor axis is just sufficient to accommodate the largest of said elements, one of said opposing sides is concave and the other opposing side is convex.

2. An improvement according to claim 1 wherein the radius of curvature of each of said opposing sides is selected from between about 2 and about 3 centimeters.

3. An improvement according to claim 2 wherein the said opposing sides are approximately parallel each other.

4. An arthroscope comprising an instrument channel, an irrigation channel, a lens system and optic fibers contained within a sheath having a cross-sectional configuration defined by a pair of approximately parallel longer sides and a pair of shorter sides configurated to contain said instrument channel, irrigation channel and lens system in approximately side-by-side lineal arrangement with said optic fibers packed in approximately longitudinal alignment therewith in the interstices between them.

5. An arthroscope according to claim 4 wherein the distal end of said sheath has a minor axis and a major axis, and the distance measured across said distal end normal its major axis is no more than approximately 3½ millimeters.

6. An arthroscope according to claim 5 wherein the side walls of said sheath intersecting its minor axis are slightly arcuate.

7. An arthroscope according to claim 6 wherein the arcuate side walls are curved along a radius of approximately 2.5 centimeters.

8. An arthroscope comprising a sheath with a cross-section having a relatively long major axis and a minor axis housing components, including optic fibers and a pair of lens systems spaced along said major axis and approximately parallel the longitudinal axis of said sheath, with said optic fibers packed in the interstices between the other of said components and the interior surface of said sheath.

9. An arthroscope according to claim 8 wherein said components include an irrigation channel.

10. An arthroscope according to claim 9 wherein said components further include an instrument channel.

11. An arthroscope according to claim 8 wherein said sheath is rigid and has a cross-sectional configuration, as viewed from its distal end, shaped approximately as a parallelogram.

12. An arthroscope according to claim 11 wherein said configuration is defined by a pair of approximately parallel longer sides and a pair of shorter sides.

13. In an arthroscope with structural elements including an optical system and a lighting system contained within a rigid sheath, the improvement which comprises providing said sheath with a cross-sectional configuration, as viewed from its distal end, having major and minor axes intersecting at the geometric center of said cross-section, wherein the opposing sides of said cross-section intersecting said minor axes are each arcuate on a radius selected to approximately match the contours of adjacent bone surfaces comprising a joint, the dimensions of the cross-section of the interior of the sheath along the said minor axis is just sufficient to accommodate the largest of said elements, one of said opposing sides is concave and the other opposing side is convex.

14. An improvement according to claim 13 wherein the radius of curvature of each of said opposing sides is selected from between about 2 and about 3 centimeters.

15. An improvement according to claim 14 wherein the said opposing sides are approximately parallel each other.

16. In an arthroscope with structural elements, including a lens system and a fiber optic lighting system, fixed within a rigid sheath, the improvement which comprises providing said sheath with a cross-sectional configuration, as viewed from its distal end, defined by a pair of approximately parallel longer sides and a pair of shorter sides, having major and minor axes intersecting at the geometric center of said cross-section, wherein the dimension of the cross-section of the interior of the sheath along the said minor axis is just sufficient to accommodate the largest of said elements.

17. An improvement according to claim 16 including an irrigation system element fixed within said sheath in approximately parllel longitudinal alignment with said other structural elements.

18. An improvement according to claim 16 wherein said lighting system includes optic fibers arranged within the interstitial spaces between elements contained within a sheath and the side walls of the sheath.

19. An improvement according to claim 18 including a lens system element and an irrigation system element in side-by-side relationship along approximately the said major axis.

20. The improvement of claim 1 wherein the opposing sides of said cross-section intersecting said minor axis are each arcuate on a radius selected to approximately match the contours of adjacent bone surfaces comprising a joint.

* * * * *